US010513720B2

(12) United States Patent
Cinti

(10) Patent No.: US 10,513,720 B2
(45) Date of Patent: Dec. 24, 2019

(54) METHOD FOR THE PRODUCTION OF DEXTRAN

(71) Applicant: BIO-E.R.G. S.R.L., Jesi (AN) (IT)

(72) Inventor: Giulia Cinti, Ancona (IT)

(73) Assignee: BIO-E.R.G. S.R.L., Jesi (An) (IT)

( * ) Notice: Subject to any disclaimer, the term of this patent is extended or adjusted under 35 U.S.C. 154(b) by 303 days.

(21) Appl. No.: 15/117,351

(22) PCT Filed: Feb. 10, 2014

(86) PCT No.: PCT/EP2014/000360
§ 371 (c)(1),
(2) Date: Aug. 8, 2016

(87) PCT Pub. No.: WO2015/117624
PCT Pub. Date: Aug. 13, 2015

(65) Prior Publication Data
US 2016/0348140 A1 Dec. 1, 2016

(51) Int. Cl.
C12P 19/08 (2006.01)
A23C 19/05 (2006.01)
C12R 1/01 (2006.01)
A23L 29/269 (2016.01)
C08B 37/02 (2006.01)
C12N 1/20 (2006.01)
C12N 9/10 (2006.01)

(52) U.S. Cl.
CPC ............ *C12P 19/08* (2013.01); *A23C 19/054* (2013.01); *A23L 29/273* (2016.08); *C08B 37/0021* (2013.01); *C12N 1/20* (2013.01); *C12N 9/1051* (2013.01); *C12R 1/01* (2013.01); *C12Y 204/01005* (2013.01); *A23V 2002/00* (2013.01)

(58) Field of Classification Search
CPC .... C12P 19/08; C12Y 204/01005; C12R 1/01
See application file for complete search history.

(56) References Cited

U.S. PATENT DOCUMENTS 5,902,800 A 5/1999 Green et al.

FOREIGN PATENT DOCUMENTS

EP 0363633 A1 4/1990
WO 03008618 A2 1/2003

OTHER PUBLICATIONS

Cagno et al., "Glucan and Fructan Production by Sourdough *Weissella cibaria* and *Lactobacillus plantarum*" J. Agric. Food Chem. 2006, 54, 9873-9881.*

Amari et al., "Characterization of a novel dextransucrase from *Weissella confusa* isolated from sourdough", Applied Microbiology and Biotechnology, 2013, vol. 97, pp. 5413-5422.
Bejar et al., "Characterization of glucansucrase and dextran from *Weissella* sp. TNB1O with potential as safe food additives", International Journal of Biological Macromolecules, 2013, vol. 52, pp. 125-132.
Rao et al., "Purification, optimization of assay, and stability studies of dextransucrase isolated from *Weissella cibaria* JAG8", Preparative Biochemistry & Biotechnology, 2013, vol. 43, pp. 329-341.
Wolter et al., "Influence of dextran-producing *Weissella cibaria* on baking properties and sensory profile of gluten-free and wheat breads", International Journal of Food Microbiology, 2013, vol. 172, pp. 83-91.
Ahmed et al., Characterization of high molecular weight dextran produced by *Weissella cibaria* CMGDEX3, Carbohydrate Polymers, 2012, vol. 90, pp. 441-446.
Bounaix et al.,"Characterization of dextran-producing *Weissella* strains isolated from sourdoughs and evidence of constitutive dextransucrase expression", FEMS Microbiology Letters, 2010, vol. 311, pp. 18-26.
Trias et al., "Lactic acid bacteria from fresh fruit and vegetables as biocontrol agents of phytopathogenic bacteria and fungi", International Microbiology, 2008, vol. 11, pp. 231-236.
Galle et al., "Exopolysaccharide forming *Weissella* strains as starter cultures for sorghum and wheat sourdoughs", 2010, Database accession No. D5H3E4.
International Search Report and Written Opinion for International Application No. PCT/EP2014/000360. (dated Sep. 29, 2014)( 17 pages).
Lynch et al., "Isolation and characterisation of exopolysaccharide-producing *Weissella* and *Lactobacillus* .and their application as adjunct cultures in Cheddar cheese", International Dairy Journal, 2014, No. 34, pp. 125-134.
"*Weissella cibaria* partial gts gene for glucansucrase, isolate F28", GenBank: FN706438.1, 1 page.
Office Action for Corresponding Japanese Patent Application No. 2016-568108 (22 Pages) (dated Dec. 4, 2017) and English language translation.
Office Action for Corresponding Japanese Patent Application No. 2016-568108 (6 Pages) (dated Oct. 29, 2018) and English language translation.

* cited by examiner

*Primary Examiner* — Louise W Humphrey
*Assistant Examiner* — Stephen A Perkins
(74) *Attorney, Agent, or Firm* — Lucas & Mercanti, LLP

(57) ABSTRACT

Method for the production of dextran comprising the following steps: prepare a culture medium containing the appropriated mixture and balance of ingredients, mainly after accurate selection of nature and concentration of carbon and nitrogen sources, with a specific initial pH, inoculate the culture medium with an appropriated quantity of bacteria strain (to standardize the production and avoid as much as possible the variability of the system); carry out the fermentation for a given time and at a given temperature; precipitate the dextran to separate the product from the culture medium; the bacteria strain is a strain of *Weissella cibaria*.

11 Claims, No Drawings
Specification includes a Sequence Listing.

METHOD FOR THE PRODUCTION OF DEXTRAN

CROSS-REFERENCE TO RELATED APPLICATIONS

This application is a 371 of PCT/EP2014/000360, filed Feb. 10, 2014, which is incorporated herein by reference

FIELD OF THE INVENTION

The present invention relates to a method for the production of dextran, and particularly relates to an optimized biosynthesis method of dextran.

BACKGROUND OF THE INVENTION

Dextran is a polysaccharide formed of glucose units, the chain lengthening of which is catalyzed by dextransucrase. Dextran is an α-D-1,6-glucose-linked glucan with variable side-chains 1-3 linked to the backbone units of the dextran polymer; this product should has different molecular weights (≥1000 Da), which influence characteristics of final solutions. The chemical and physical properties of native dextran powder change in function of the microbial strain from which it is produced and/or by the production method. The biosynthesis of dextran has been demonstrated in numerous bacteria, especially in *Streptococcus mutans, Leuconostoc mesenteroides* ssp. *mesenteroides* and *Leuconostoc mesenteroides* ssp. *dextranicum*. *Leuconostoc* produces the enzyme dextransucrase and secrete it into the culture medium in the presence of sucrose. This enzyme, dextransucrase, synthesizes dextran from the sucrose substrate, catalyzing the transfer of glucosyl residues from sucrose to dextran polymer and liberating fructose. The origin of the dextransucrase (i.e. the producing microorganism) influences the frequency and nature of the branch points of dextran molecule.

Dextran is an easily soluble, biocompatible and biodegradable polymer; commercial native dextran powder has applications in several fields. It is used especially in biochemistry as a support for filtration chromatography on a gel of the Sephadex type. Dextran could be used in cosmetic industry and in pharmaceutical compositions (see for example U.S. Pat. No. 5,902,800). Additionally, in the field of therapeutics, it is used as a substitute for blood plasma (Biochimie generale (General Biochemistry)—J. H. WEIL-Masson, 6th edition-1990-p. 171). Furthermore, dextran synthesized by a strain of *Leuconostoc dextranicum* is applied in the food industry for the texturing of food products such as yoghurts, cream desserts, milk-based drinks and salad dressings. European Patent Application Publication No. EP0363633 demonstrates the synthesis of dextran by a strain of *Leuconostoc dextranicum* and in particular by the strain *Leuconostoc dextranicum* NRRL-B-18242. Additionally, that patent application publication describes especially a composition containing dextran synthesized by this bacterium and the use of this composition in the food sector. The food application of dextran follows the trend of customers who want to prepare foods to be authentic, tasty and natural, turning away from those containing chemical additives. Natural additives—obtained trough fermentation—respond to food producers requests for natural options for ingredients, which result safe, reliable and sustainable. Dextran powder should be also utilized in bakery, as texturing agent, mainly in gluten-free sourdough, enhancing technical performances of the final products. At this proposal, high molecular weight dextrans (1-2·10$^6$ Da) have been approved by the European Union as a food ingredients in bakery products (Naessens M. et al., 2005).

Presently, searching for a bacterium, which is able to achieve high yields of heavy molecular weight dextran, is addressed to a species known as *Weissella cibaria*. *W. cibaria* is a species of Gram-positive, heterofermentative bacteria, placed within the family of Leuconostocaceae, which has been defined in 2002 (Björkroth K J, Schillinger U, Geisen R, et al., January 2002). "*Taxonomic study of Weissella confusa and description of Weissella cibaria sp. nov., detected in food and clinical samples*". International Journal of Systematic and Evolutionary Microbiology 52 (Pt 1): 141-8). *W. cibaria* is a GRAS bacterium (Generally Recognized As Safe) by the United States Food and Drug Administration (FDA) and the genera is also included in the list of taxonomic units proposed by the European Food Safety Authority (EFSA, QPS list, Qualified Presumption of Safety). This strain should have a great importance because of many industrial applications. This species was isolated from a natural substrate and then it was selected after slime formation from sucrose. It has also been found to be hyper-productive in terms of dextran synthesis from sucrose.

The above strain of *Weissella cibaria* was accepted as a patent deposit under Accession Number 42196 at the NCIMB, Ltd International Depositories, located at Ferguson Building, Craibstone Estate, Bucksburn Aberdeen, AB21 9YA, Scotland UK, on Nov. 28, 2013.

OBJECT OF THE INVENTION

A first aim of the research leading to the present invention is to isolate a microrganism from a natural food substrate and to identify this bacteria strain which is able to produce dextran with high yields, and particularly a strain from the species of *Weissella cibaria*. Another aim of the present invention is to provide a personalized method for the production of dextran which enables the production, with high yields, of an heavy molecular weight dextran powder.

An object of the present invention is therefore a tailored method for the production of dextran comprising the steps of:

- Prepare an optimized synthetic culture medium containing the right balance of nutrients, selecting especially the appropriated (in terms of nature and concentration) carbon and nitrogen sources, having a given pH (after fine-tuning experiments for this process);
- Guarantee a good growth-rate with a suitable (in terms of age and amount) inoculum size of the bacterium pre-culture (lyophilized after arriving at exponential phase to standardize the procedure);
- Carry out the incubation for a given time; at a given optimal temperature (because high temperatures should decrease cell growth and lead to a partial instability of the enzyme).
- Separate the synthesized dextran from the culture medium optimizing the downstream recovery of the product and increasing at most yields.

All above described steps are optimized for the bacteria strain *Weissella cibaria* as from the deposit No. NCIMB 42196 (November 2013). This strain is non-spore-forming, non-motile, microaerophile, heterofermentative and catalase negative, produces acid form L-arabinose but not from galactose.

An object of the present invention is a strain of *Weissella cibaria*, as according to the deposit No. NCIMB 42196, for the production of high molecular weight dextran.

In a preferred embodiment of the invention, the best nitrogen source for dextran production is yeast extract, in a percentage of about 1% to 2% w/v. The carbon source is mainly sucrose, in a percentage from 10% to 15% w/v.

In another embodiment of the invention, the culture medium contains also enriched scotta-broth, or similar by-product of cheese industry, in a percentage from about 80% to about 90%. Scotta-broth is a variable substrate made essentially by salts and minerals (which remain after the ricotta-cheese making process). The composition of this natural food substrate usually changes in function of production steps and characteristics of raw material (cow milk).

The initial pH value of the culture medium will be better adjusted around of pH 6-7, and preferably it is about pH 6.5.

The incubation time is comprised between 20 and 36 hours, and preferably will be of 24 hours. The incubation is carried out under slight agitation, at about 50 rpm.

The incubation is carried out at about 28° C. to 32° C., and preferably at 30° C.

Another object is the dextransucrase produced by the bacterium of the strain of *Weissella cibaria* as above referred. The genomic sequence and the protein sequence of said dextransucrase has been detected and listed, and is appended to the present application.

A further object of the present invention is an high molecular weight (between $5 \cdot 10^6$ and $4 \cdot 10^7$ Da) dextran powder obtained according to method as referred to above. This dextran powder has a protein content comprised between 7% and 11%, and mainly of the 9% and the characteristic viscosity values of dextran solutions are between 4.0 and 5.0 mPa·s (at a temperature of 20° C.-25° C.), obtained according to the method of the present invention is comprised.

DESCRIPTION OF SOME EMBODIMENTS OF THE INVENTION

Literature shows many examples of variability in dextran production due to various process parameters affected microbial biosynthesis. The isolation of a dextran-producing micro-organisms with potential for industrial applications and the identification of the optimal combination of factors that affect dextran production represent the two main foci of this work.

To provide high yields using suitable medium composition (in terms of essential nutritional requirements and adapted variables) and optimized process parameters (in terms of industrial scale production using a specific strain of Lactic Acid Bacteria), there were performed experiments on shaking-flasks (500 ml) and in batch fermentation (without pH control).

For all experiments was used an inoculum of our lyophilized strain of *Weissella cibaria* according to the deposit No. NCIMB 42196 ($6 \cdot 10^7$ CFU/ml) after 18-20 hours of growth in MRS medium at 30° C. (added quantity: 1/200 w/v) and dextran was determined by precipitation in ethanol and dried at 100° C.

Example 1. Effect of Nitrogen Source and Concentration on Dextran Production Maintaining constant the sucrose concentration (10% w/v), the purpose was to verify if dextran production should be influenced by nitrogen (and other salts) availability. After testing some media enriched in phosphate and nitrogen sources and concentration and other poor respect to these types of nutrients (or their combinations), we found out that dextran production was sensibly influenced by nitrogen source and yeast extract was the best nutrient source (between the tested ones). Considering that yeast extract is obtained from autolysis of yeast cells (*Saccharomyces*) and it is a good source of amino-nitrogen and vitamins, particularly the water soluble B-complex vitamins, it guaranteed good cell growth in quite short times (despite of other tested sources). Additionally, yeast extract, combined with some other salts (see further examples), gave the best balance of nutrients in order to promote cell proliferation.

Medium 1a (peptone 1% w/v, sucrose 10% w/v)
Medium 1b (peptone 2%, sucrose 10%)
Medium 2a (yeast extract 1%, sucrose 10%)
Medium 2b (yeast extract 1.5%, sucrose 10%)
Medium 2c (yeast extract 2%, sucrose 10%)
Medium 3 (ammonium nitrate 1%, sucrose 10%)
Medium 4 (ammonium sulphate 1%, sucrose 10%)
Medium 5 (ammonium chloride 0.5%, potassium nitrate 0.5% and sodium nitrate 0.5%, sucrose 10%)
Medium Dextran (g/100 ml) Percent conversion of sucrose

| | | |
|---|---|---|
| 1a | 3.5 ± 0.2 | 35% |
| 1b | 3.8 ± 0.05 | 38% |
| 2a | 5.1 ± 0.02 | 51% |
| 2b | 6.0 ± 0.05 | 60% |
| 2c | 6.2 ± 0.1 | 62% |
| 3 | 2.5 ± 0.2 | 25% |
| 4 | 2.8 ± 0.05 | 28% |
| 5 | 3.0 ± 0.08 | 30% |

Different Nitrogen sources (simple salts or complex substrates) did not allow to the same dextran production (in terms of final yields) and the highest amount of dextran was related to the introduction of yeast extract (from 1% to 2%, with the maximum conversion percentage of sucrose at 1.5%), which increased also cell growth (decreasing time of production). In other words, the yeast extract concentration of about 1.5% revealed the best compromise between bacteria cell growth and product formation (during further experiments this basal medium was enriched using some other nutrient sources to maximize the yields).

Example 2. Effect of Nature and Concentration of Carbon Source on Dextran Production Maintaining constant the selected nitrogen source (yeast extract), the aim was to verify the effect of different carbon sources (alternative to sucrose) on dextran production. In each medium 5% w/v of sucrose was added. Sucrose was added with alternative carbon sources: corn steep liquor, glucose, fructose, mannose, lactose (1.5% w/v of yeast extract was added in each medium).

Medium 1: corn steep liquor 5% (1a) and 10% (1b)+sucrose 5%
Medium 2: glucose 10% w/v+sucrose 5% w/v
Medium 3: mannose 10%+sucrose 5%
Medium 4: lactose 10%+sucrose 5%
Medium Dextran (g/100 ml)

| | |
|---|---|
| 1a | 1.6 ± 0.1 |
| 1b | 1.5 ± 0.3 |
| 2 | 3.2 ± 0.1 |
| 3 | 3.3 ± 0.2 |
| 4 | 3.1 ± 0.1 |

The dextran production was always and indiscriminately low in presence of different carbon sources alternative to sucrose. This strain uses sucrose as the sole carbohydrate source for dextran production (as reported for other species such as L. mesenteroides—Cavenaghi, 2000). Sucrose seem to be an inducer of dextran production related to other tested carbon sources (due to induction of specific enzyme). Also mixing two different carbon sources does not increase significantly the production of dextran.

Example 3. Effect of Sucrose Concentration on Dextran Production

Maintaining constant yeast extract concentration (1.5% w/v) and using sucrose as the only available carbon source, the aim was to determine the influence of substrate concentration on dextran production.
Medium 1: 5% w/v sucrose
Medium 2: 10% sucrose
Medium 3: 15% sucrose
Medium 4: 20% sucrose
Medium 5: 25% sucrose
Medium Dextran (g) Percent conversion of sucrose

| | | |
|---|---|---|
| 1 | 3.8 ± 0.2 | 76% |
| 2 | 5.9 ± 0.3 | 59% |
| 3 | 6.1 ± 0.08 | 40.7% |
| 4 | 6.0 ± 0.1 | 30% |
| 5 | 5.8 ± 0.07* | 23.2% |

*high residue sucrose

At the higher initial concentration of sucrose, the higher yields of dextran was obtained per unit volume. As a result, the best compromise between growth rate, dextran production and time of conversion (also considering percent conversion of sucrose, without substrate residue) was obtained using 10-15% (w/v) of sucrose. Maximum specific growth rate ($\mu_{MAX}$) under optimal experimental conditions (pH 6.5, temperature 30° C., yeast extract 1.5% w/v and other added salts, right inoculum size) was estimated around 0.94 $h^{-1}$.

Example 4. Effect of Initial pH on Dextran Production

MRS medium (supplemented by sucrose until final concentration of 15% w/v) was used for these experiments. Best initial pH (before sterilization, adjusted using NaOH 1M), in terms of effect on cell growth and final dextran production, was between 6.0-7.0 (with the optimal result at 6.5).
The final pH of culture (at the end of fermentation) is of about 3.5.

Example 5. Effect of Agitation Speed (Stirring) on Dextran Production

Flasks containing MRS medium (supplemented by sucrose until final concentration of 15% w/v) were used for these experiments. There were performed some experiments using different agitation speed (50, 100, 150, 200, 250, 300 rpm). Results found that dextran production was not greatly influenced by agitation speed, so to reduce foam risk and to save energy during the process, the best agitation speed was selected at 50 rpm.
The strain is facultative microaerophile and the experimental evidences confirm that oxygen availability should positively affects the growth of the strain but does not influence significantly the production of dextran. The aerobic condition used during fermentation experiments (in 20 l bioreactor) was an oxygen transfer rate of about 1.0 mmol/l·h.

Example 6. Effect of Inoculum Size on Dextran Production

Flasks containing MRS medium (supplemented by sucrose until final concentration of 15% w/v) was used for these experiments.
For all experiments was used an inoculum of our lyophilized strain (6·$10^7$ CFU/ml) after 18-20 hours of growth in synthetic medium (Sucrose 10-15% w/v, Yeast Extract 1.5% w/v, $K_2HPO_4$ 0.4% w/v, Sodium Acetate·$3H_2O$ 1% w/v, Citric Acid 0.4% w/v, $MgSO_4·7H_2O$ 0.05% w/v) at 30° C. (added quantities for inoculum: 1/100 w/v, 1/200 w/v, 1/250 w/v, 1/300 w/v).

| Inoculum Size | Dextran (g/L) |
|---|---|
| 1 | 49.5 ± 0.1 |
| 2 | 58.3 ± 0.07 |
| 3 | 60.2 ± 0.2 |
| 4 | 48.8 ± 0.1 |

Inoculum size mainly affected the fermentation time and the best experimental result (in terms of standardization of cell growth, fermentation time and dextran production) was obtained using a dilution of 1/200 w/v of lyophilized cells of W. cibaria strain.

Example 7. Effect of Incubation Time on Dextran Production

Flasks containing MRS medium (supplemented by sucrose until final concentration of 15% w/v) was used for these experiments. To determine dextran production it has to be considered that bacterial cells had to pass the lag phase and to adapt to the medium and had to grow until carbon source (and other nutrients) are still available. For these reasons incubation time was followed in the range of 16 to 36 hours in order to find out the best dextran production.
Incubation time of 24 hours (at most 36 hours) was found to be the optimum incubation time. Anyway, the production process should be controlled by a double check: the increasing viscosity of the medium and the decrease of pH during fermentation.
The final complex and synthetic medium composition (in water), to maximize growth rate and to maintain the highest standard of dextran production (in at least 24/36 hours):
Sucrose 10-15% wt (145 g/l)
Yeast Extract 1.5% wt (10-15 g/l)
$K_2HPO_4$ 0.4% wt (4 g/l)
Sodium Acetate·$3H_2O$ 1% wt (10 g/l)
Citric Acid 0.4% wt (4 g/l)
$MgSO_4·7H_2O$ 0.05% wt (0.5 g/l)
pH 6.0 7.0
Temperature: 30° C.
Fermentation time: 24 hours (maximum 36 hours)
Inoculum size: 1/200 w/v of lyophilized cells (6·$10^7$ CFU/ml, after 18-20 hours at 30° C. in MRS medium)
Dextran is a neutral and water soluble polysaccharide, for this reason the viscosity is not significantly influenced by changes in pH or salt concentration. Dextran is a neutral polymer with large dimensions, so it will not easily pass/diffuse trough human cells and tissues, maintaining a favorable osmotic pressure. Dynamic rheological experiments (on the bottom plate of the rheometer) and the viscosity of dextran-water solutions (at different concentrations, pH 6.5) was measured (the viscosity of all solutions is independent on the shear rate because the property of ideal-viscous liquid) and the final viscosity of a 15% dextran-water solution is about 210 η (mPa*s) and of a 1% dextran-final solution is about 5 η (mPa*s).

Another possible food application of high molecular weight dextran involved cheese production and is based on the property of dextran which should be a good fat-replacer. Many commercial fat-replacers (based, for example, on whey-proteins, starch and xanthan gum or microcrystalline cellulose) are already known for potential to make superior low-fat products; most of them are based on micro-particulated material and require high costs of production.

The same strain of *W. cibaria* (deposit n. NCIMB 42196) was used to inoculate synthetic medium based on scotta-broth, enriched with sucrose and other salts. The aim of this second part of the project was to recovery a by-product of dairy industry in order to avoid costs of getting off the by-product and to improve the food product quality. Scotta-broth is a substrate derived from ricotta cheese production process and it is a variable by-product, in terms of salts and nutrient composition.

Scotta-broth usually contains low level of proteins (0.10-0.15%) and high concentration of salts (0.9-1.2%) and organic acids (0.20-0.25%); fats are around 0.15-0.30% and low levels of residual lactose. Fermenting synthetic media based on scotta-broth (enriched by sucrose and yeast extract as shown below), it is possible to obtain a viscous naturally fermented fluid, which in turn could be include in further cheese-making productions and which it is called dextran-paste (naturally enriched in dextran during fermentation, with a final concentration of 8-10%). This could be an opportunity to increase the value of this by-products and to enrich the healthy properties of the final product (without changing any step of the actual process).

Simply adding the fermented dextran-paste to the raw milk during cheese production (characterized by a viscosity of about 600-700 cp, due to natural accumulation of dextran during fermentation), it is possible to increase yields of production and to realize low-fat cheese (until final concentration of 4-5% fats, as reported in the US food labeling requirements of ≤3 g fat/50 g of the reference amount for low-fat foods).

Fermented dextran-paste should be directly incorporated into the cheese matrix following the concept of clean labeling (without any declaration about addiction of other food ingredients) and it makes interactions with caseins affecting distribution on cheese structure. Characteristics and performances of low-fat cheese could be ameliorated because the water content of the cheese is increased, due to binding of water made by dextran. Fat content of cheese influences micro-structure of the product and high moisture content.

Medium Composition for Dextran Paste:
Sucrose 10-15% w/v
Yeast Extract 1-1.5% w/v
scotta-broth 83-89% w/v
About Enzyme Involved into the Dextran Synthesis:

Dextransucrase, or glucansucrase (GH 70), is an extra-cellular enzyme of glycoside hydrolase family 70, which cleave the glycosidic linkage between glucose and also often bind carbohydrate modules. This enzyme exists in single or multiple molecular forms and has different molecular weights. Metal ions such as $Ca^{2+}$, $Mg^{2+}$ and $Co^{2+}$ should increase enzyme activity and other ones such as $Cu^{2+}$, $Fe^{3+}$ and $Mn^{2+}$ inhibit dextransucrase activity (Kobayashi M. and Matsuda K., 1976: Goyal A., Nigam M. and Katiyar S. S., 1995).

The genomic sequence of the dextransucrase produced by the strain of *Weissella cibaria* according to the deposit No. NCIMB 42196 has been detected and listed, and is appended to the present application.

The invention claimed is:

1. A method for producing dextran comprising
 (a) preparing a culture medium containing a percentage of a carbon source and a percentage of a nitrogen source at an initial pH;
 (b) inoculating the culture medium with a bacteria strain of *Weissella cibaria* deposited as Accession No. NCIMB 42196;
 (c) producing dextran by fermenting the inoculated culture medium;
 (d) precipitating the inoculated culture medium; and
 (e) separating the dextran from the fermented culture medium.

2. The method according to the claim 1, wherein the nitrogen source is a yeast extract, in a percentage of from about 1% to 2% w/v of the culture medium, and the carbon source is sucrose, in a percentage from 10% to 15% w/v of the culture medium.

3. The method according to claim 1, wherein the culture medium also contains a substrate derived from ricotta cheese production in a percentage (w/v) from about 80% to about 90%, and wherein the substrate contains proteins in a percentage (w/v) of 0.10% to 0.15%, salts in a percentage (w/v) of 0.9 to 1.2%, organic acids in a percentage (w/v) of 0.20-0.25%, fats in a percentage (w/v) of 0.15% to 0.30% and residual lactose in a percentage (w/v) of 4.0% to 4.6%.

4. The method according to claim 1, further comprising the step of adjusting the initial pH of the culture medium to a pH of from 6 to 7.

5. The method according to claim 1, wherein the fermenting time is between 20 and 36 hours.

6. The method according to claim 1, wherein the fermenting is carried out under slight agitation, at about 50 rpm.

7. The method according to claim 1, wherein the fermenting is carried out at a temperature of about 25° C. to 35° C.

8. A strain of *Weissella cibaria*, deposited as Accession No. NCIMB 42196, for the production of dextran.

9. The method according to claim 4, wherein the pH of the culture medium is adjusted to about 6.5.

10. The method according to claim 5, wherein the fermenting time is 24 hours.

11. The method according to claim 7, wherein the fermenting is carried out at a temperature of about 30° C.

\* \* \* \* \*

SEQUENCE LISTING

<160> NUMBER OF SEQ ID NOS: 1

<210> SEQ ID NO 1
<211> LENGTH: 1133
<212> TYPE: DNA
<213> ORGANISM: Weissella cibaria No. NCIMB 42196

<400> SEQUENCE: 1

```
ctatttactc gtttgtgcgt gcccatgata gcgaagtaca aacagtcatt gctgagatcg    60
tgacgaagct gcatccagaa gcaggaaatg ggttaatgcc tacggaagaa caaatggcag   120
aagcgtttaa gatttacaat gcggaccaaa agaaggccgt taagacttac acacattaca   180
atatgccatc tgcatacgcc atgctgttaa cgaacaagga tgttattcca cgaatttact   240
atggtgactt gtacactgat gatgggcaat tcatggcgac aaaatcacct tattttgatg   300
cgatttcgac catgttacaa gcacgcacga agtatgtaac tggtggacag acgtatatgc   360
acacacagtt gatttggtca ttaaccaagc ccgaggcaca acgcgggacc atggcacgct   420
ttatggactt ctatctcacc aaccgtgcta atgatgatac agaaaacacg gcgcaaccta   480
gttactcgtt tgtgcgtgcc catgatagcg aagtacaaac agtcattgct gagatcgtga   540
cgaagctgca tccagaagca ggaaatgggt taatgcctac ggaagaacaa atggcagaag   600
cgtttaagat ttacaatgcg gaccaaaaga aggccgttaa gacttacaca cattacaata   660
```

```
tgccatctgc atacgccatg ctgttaacga acaaggatgt tattccacga atttactatg       720
gtgacttgta cactgatgat gggcaattca tggcgacaaa atcaccttat tttgatgcga       780
tttcgaccat gttacaagca cgcacgaagt atgtaactgg tggacagacg atggcggttg       840
accagcacga cgtcttgact agcgttcggt ttggtaaggg ggccatgacg gccaatgatt       900
taggggatgc tgagacccgg actgagggtg tgggattaat tattagcaac aacccaaagt       960
tgcaattggg acaacaagac aacgtggtgt tacacatggg acttgcgcac gcgaatcagg      1020
cattccgcgc agtcgtacta acgaccgcga ccggattaac catttataat gacgatgatg      1080
ctccaattcg ttataccgat aataagggtg atttaatttt cactaaccat gac            1133
```